US011295835B2

(12) United States Patent
Ingel et al.

(10) Patent No.: US 11,295,835 B2
(45) Date of Patent: Apr. 5, 2022

(54) SYSTEM AND METHOD FOR INTERACTIVE EVENT TIMELINE

(71) Applicant: Biosense Webster (Israel) Ltd., Yokneam (IL)

(72) Inventors: Moshe Ingel, Haifa (IL); Oshrat Ben Zaken, Shimshit (IL); Ben Ami Novogrodsky, Yokneam (IL); Toam Shemesh, Herzliya (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 511 days.

(21) Appl. No.: 15/823,164

(22) Filed: Nov. 27, 2017

(65) Prior Publication Data
US 2019/0164633 A1 May 30, 2019

(51) Int. Cl.
*G16H 10/60* (2018.01)
*A61B 5/0205* (2006.01)
(Continued)

(52) U.S. Cl.
CPC .......... *G16H 10/60* (2018.01); *A61B 5/0205* (2013.01); *A61B 5/339* (2021.01); *A61B 5/4848* (2013.01);
(Continued)

(58) Field of Classification Search
CPC .. G06Q 50/22–24; G16H 10/60; G16H 50/50; G16H 30/40; G16H 20/40; G16H 30/20; G16H 40/63; A61B 5/4848; A61B 5/044; A61B 5/7435; A61B 5/0205; A61B 5/0422; A61B 2505/05; A61B 34/20; A61B 18/12; A61B 18/14; A61B 2034/2051;
(Continued)

(56) References Cited

U.S. PATENT DOCUMENTS

2007/0055142 A1* 3/2007 Webler .................. A61B 5/062 600/425
2007/0167801 A1* 7/2007 Webler .................. A61B 8/445 600/459
(Continued)

FOREIGN PATENT DOCUMENTS

WO 2008/138009 A1 11/2008

OTHER PUBLICATIONS

Extended European Search Report dated Aug. 2, 2019 for the European Patent Application No. 18208353.5.

*Primary Examiner* — Mark Holcomb
(74) *Attorney, Agent, or Firm* — Volpe Koenig (57) ABSTRACT

An interactive event timeline system and method are disclosed. Multiple events and/or signal indicators are captured during a medical procedure, such as a cardiac procedure. Event data relevant to the cardiac procedure may include, tags, user generated points, ablation events, pacing events and other like events. An interactive event timeline is generated from the captured events and displayed on a visual display device. The interactive event timeline is correlated with a vertical listing of the events and a selected event viewer. All three views may be displayed simultaneously. The interactive event timeline allows a physician or user (collectively "user") to see temporal relationships between the captured events. The user can see, for example, simultaneous events, long duration events versus short duration events, continuous events and specific event types.

17 Claims, 6 Drawing Sheets

(51) Int. Cl.
*G16H 30/20* (2018.01)
*G16H 50/50* (2018.01)
*G16H 30/40* (2018.01)
*G16H 20/40* (2018.01)
*A61B 5/00* (2006.01)
*A61B 5/339* (2021.01)
*A61B 5/287* (2021.01)

(52) U.S. Cl.
CPC ........... *A61B 5/7435* (2013.01); *G16H 20/40* (2018.01); *G16H 30/20* (2018.01); *G16H 30/40* (2018.01); *G16H 50/50* (2018.01); *A61B 5/287* (2021.01); *A61B 2505/05* (2013.01)

(58) Field of Classification Search
CPC .... A61B 2034/2072; A61B 2034/2065; A61B 2018/147; A61B 2018/00791; A61B 2018/00351; A61B 2018/00577; A61B 2576/023

USPC .......................... 705/2–4; 715/780, 792, 800
See application file for complete search history.

(56) References Cited

U.S. PATENT DOCUMENTS

| | | | |
|---|---|---|---|
| 2009/0069704 A1* | 3/2009 | MacAdam | G06T 7/0012 600/523 |
| 2010/0131293 A1* | 5/2010 | Linthicum | G06Q 50/24 705/3 |
| 2013/0179191 A1* | 7/2013 | Bal | G16H 10/60 705/3 |
| 2016/0331262 A1 | 11/2016 | Kuck et al. | |
| 2017/0116373 A1* | 4/2017 | Ginsburg | G16H 40/20 |
| 2017/0300653 A1 | 10/2017 | Hresko et al. | |
| 2018/0292978 A1* | 10/2018 | Davies | G06F 3/04845 |

* cited by examiner

SYSTEM AND METHOD FOR INTERACTIVE EVENT TIMELINE

SUMMARY

An interactive event timeline system and method are disclosed. Multiple events and signal indicators are captured during a medical procedure, such as a cardiac procedure. Event data relevant to the cardiac procedure may include, tags, user generated points, ablation events, pacing events and other like events. An interactive event timeline is generated from the captured events and displayed on a visual display device. In an implementation, the interactive event timeline is a horizontal event timeline. The interactive event timeline is correlated with a vertical listing of the events and a selected event viewer. All three views may be displayed simultaneously. The interactive event timeline allows a physician or user (collectively "user") to see temporal relationships between the captured events. The user can see, for example, simultaneous events, long duration events versus short duration events, continuous events and specific event types. A selection of an event allows the user to see the signal indicators acquired at that time.

The interactive event timeline enables the user to review events from specific parts of the medical procedure. The physician can easily navigate between events of various types that occur throughout the procedure, analyze them, mark them and retroactively define them. This allows the physician to easily reach and define points of interest during the procedure and understand the immediate context of the situation, such as what happened right before and after a specific event, in terms of signal indicators. That is, the interactive timeline functions according to the analysis of signal indicators. For example, the interactive event timeline enables the physician to highlight clinical events in their time and electrograms context, and enables the physician to quickly navigate, understand, mark, and retroactively define key points of interest to improve accuracy and patient outcomes. The interactive event timeline can be zoomed in and out to enable different resolutions of time scope, and also to enable the physician to obtain a high level view of the procedure events as well as drill down to analyze points of interest.

BRIEF DESCRIPTION OF THE DRAWINGS

The patent or application file contains at least one color drawing or photograph as a drawing executed in color. Copies of this patent or patent application publication with color drawing(s) will be provided by the Office upon request and payment of the necessary fee.

DETAILED DESCRIPTION OF THE EMBODIMENTS

Cardiac ablation is a medical procedure performed by electrophysiologists that may be used to correct heart rhythm defects, known as arrhythmias, by creating lesions to destroy tissue in the heart that contributes to the rhythm defects. An example arrhythmia that can be treated using cardiac ablation is atrial fibrillation (AF), which is an abnormal heart rhythm that originates in the atria of the heart.

Cardiac ablation may employ long, flexible catheters that may be inserted through a small incision in the groin and through the blood vessels to the heart, and may be used to apply energy (e.g., radio frequency (RF) energy, or extreme cold) to produce small scars or lesions on the tissue to block faulty electrical impulses that may cause the heart rhythm disorders. Real-time three-dimensional (3D) location and mapping technology may be employed to visualize the exact position and orientation of a catheter within the heart and act as an advanced navigation system to enable the electrophysiologist to visualize and carefully guide the catheter to administer the RF energy in the appropriate locations. Goals of cardiac ablation are to remove the arrhythmia to return the patient's heart to a normal heart rhythm or reduce the frequency of arrhythmia and the severity of symptoms in the patient.

An example of a real-time 3D location and mapping system for cardiac ablation is the CARTO® 3 System, produced by Biosense Webster®, Inc., a subsidiary of Johnson & Johnson. The CARTO® 3 System uses electromagnetic technology to create 3D maps of a patient's cardiac structure and to display the exact location and orientation of the catheters (or other objects) in the heart. The CARTO® 3 System compensates for patient and cardiac motion to ensure accurate, real-time visualization of the cardiac structures.

Figure 1:
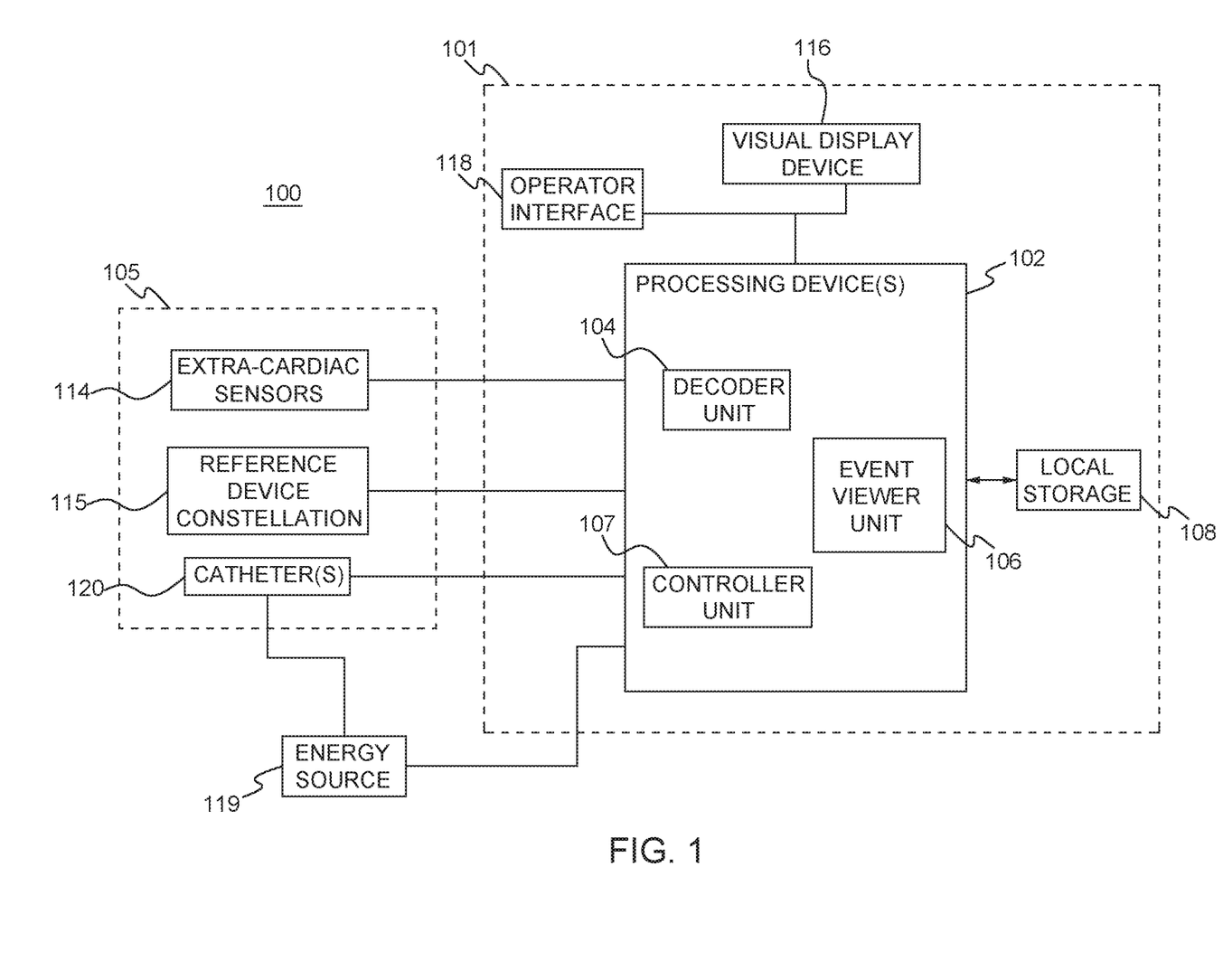
FIG. 1 is a schematic diagram of an example cardiac mapping and ablation system in accordance with certain implementations.

FIG. 1 is a schematic diagram of an example cardiac mapping and ablation system 100 with an interactive event timeline in accordance with the disclosures herein. The cardiac mapping and ablation system 100 may include, but is not limited to include, any of the following components: a console system 101; extra-cardiac sensors 114; reference device constellation 115; energy source 119; and/or catheter(s) 120. The console system 101 may include, but is not limited to include, any of the following components: processing device(s) 102 (processor(s)); local storage 108; visual display device 116; and/or operator interface(s) 118. Certain elements of the cardiac mapping and ablation system 100 may be used directly on, in, and/or in proximity to patient 105 in order to gather information to be used for visualization, diagnostics, and to perform ablation therapy. This information may be provided to console system 101 for processing, visualization and operator control and direction, some of which is described below.

Reference device constellation 115 (e.g., may be referred to as a location pad) may include a ring of computer-controlled (e.g., controlled by processing device(s) 102) magnets positioned beneath patient 105. The magnets may have known and fixed strength and position values that may be used as point of origin references for the magnetic fields in the surrounding space and may provide the reference information to processing device(s) 102 to be used in producing accurate 3D images of the heart.

Extra-cardiac sensor(s) 114 may be electrodes on the skin of a patient 105, for example. Extra-cardiac sensor(s) 114 may detect the electrical activity of the heart via detection of electrical changes on the skin due to the electro-physiologic pattern of the heart, and provide information on the electrical activity to processing device(s) 102 to be used in diagnosing arrhythmias and determining a therapeutic course of action. Processed versions of the extra-cardiac signals detected by extra-cardiac sensor(s) 114 may be displayed on visual display device 216, for example in a graphical user interface (GUI).

One or more devices may be used on patient 105 for therapeutic and diagnostic purposes. In example cardiac mapping and ablation system 100, catheter(s) 120 are shown and described for these purposes; however, other devices may be used for diagnostics and/or therapeutic treatment.

One or more catheter(s) 120 may be percutaneously inserted by a physician through patient's 105 vascular system into the heart of patient 105. Catheter(s) 120 may be equipped with a variety of sensors, such as location, electrical, pressure, image and/or temperature sensors, for the purpose of gathering information for diagnostic mapping and/or delivering therapeutic treatment (e.g., performing ablation). Different types of catheter(s) 120 may be used including, but not limited to, the following example types: fixed catheter; deflectable catheter; bi-directional catheter; uni-directional catheter; mapping catheter; halo-shaped tip catheter; basket catheter; and/or lasso-shaped catheter. When catheter(s) 120 is used for performing ablation on a target location (e.g., one or more locations along a path), for example by applying RF energy, catheter(s) 120 may receive the RF energy from energy source 119, as may be instructed by processing device(s) 102. In an example, catheter(s) 120 may request the RF energy directly from energy source 119.

Figure 2:
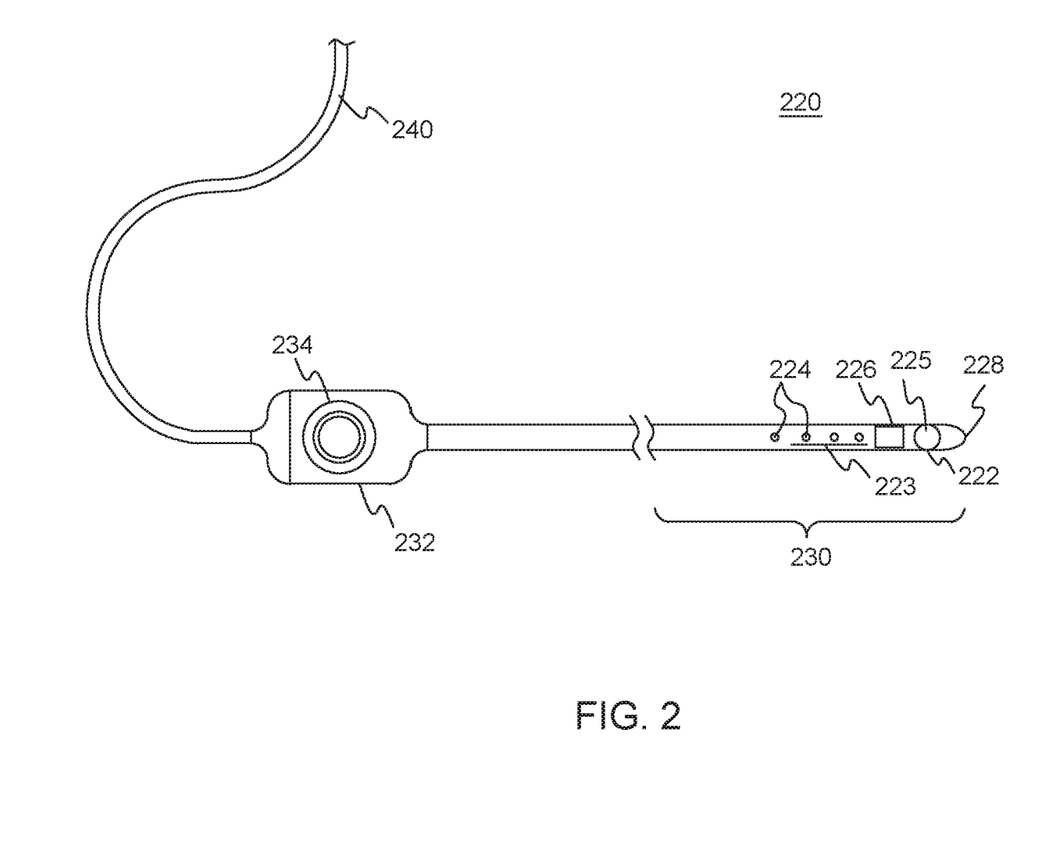
FIG. 2 is a schematic diagram of an example catheter that may be included in the example cardiac mapping and ablation system of FIG. 1 in accordance with certain implementations.

An example catheter 120 is shown in greater detail in FIG. 2, showing some, but not all, of the elements that may be included in catheter 120. A catheter 120 may include, but is not limited to include, any one or more of the following components: electrode(s) 122; temperature sensor(s) 123; non-contact electrodes 124; image sensor(s) 125; positioning sensor(s) 126; distal tip 128; distal end 130; handle 132; and/or cable 140. The schematic diagram of catheter 120 in FIG. 2 is a high-level representation of possible components of catheter 120, such that the location and configuration of the components in catheter 120 may be different than shown.

Distal end 130 of catheter 120 may include an electrode(s) 122 at distal tip 128 that may be used to measure electrical properties of the cardiac tissue. Electrode(s) 122 may also be used to send electrical signals to the heart for diagnostic purposes. Electrode(s) 122 may also perform ablation on defective cardiac tissue by applying energy (e.g., RF energy) directly to the cardiac tissue at the desired location of ablation.

Distal end 130 of catheter 120 may include temperature sensor(s) 123 to measure the temperature of the cardiac tissue in contact with distal end 130 and/or measure the temperature of the distal end 130 itself. For example, thermocouples or thermistors for measuring temperature may be placed anywhere along the distal end 130 to serve as temperature sensor(s) 123.

Distal end 130 may include non-contact electrodes 124 arranged in an array, which may be used to simultaneously receive and measure far-field electrical signals from the walls of the heart chamber of patient 105. Electrode(s) 122 and non-contact electrodes 124 provide information regarding the electrical properties of the heart to processing device(s) 102 for processing.

Catheter(s) 120 may be equipped with one or more image sensor(s) 125, such as a charge coupled device (CCD) image sensor, and/or a camera for capturing endoscopic images when inserted in a body cavity. Image sensor(s) 125 may be located at distal end 130.

Distal end 130 may include positioning sensor(s) 126 (also called location sensors) in distal tip 128 of catheter 220 that may generate signals used to determine the position and orientation (and/or distance) of catheter 120 in the body. In an example, the relative position and orientation of positioning sensor(s) 126, electrode(s) 122, and distal tip 128 are fixed and known in order to facilitate accurate positioning information of distal tip 128. For example, the position of positioning sensor(s) 126 may be determined in part based on the relative position to known positions outside the heart (e.g., based on extra-cardiac sensors 114). The use of positioning sensor(s) 126 may provide improved location accuracy within the magnetic fields in the surrounding space and provide location information that is adaptable to patient movement because the position information of catheter 120 is relative to the anatomy of the patient 205.

Handle 132 of catheter 120 may be operated by the physician and may include controls 134 to enable the physician to effectively steer distal tip 128 in the desired direction.

Electrodes 122, 124, and sensors 123, 125, 126 may be connected to processing device(s) 102 via wires that may pass through handle 132 and cable 140, in order to provide information, such as location, electrical, imaging and/or temperature information, to console system 101, which may be used to operate and display the function of catheter 120 within the heart in real-time.

With reference also to FIG. 1, within console system 101, processing device(s) 102 (e.g., processor(s)) may include one or more signal processing circuits that may be contained inside a computer, for example. Processing device(s) 102 may be implemented in hardware and/or programmed in software to carry out the functions of cardiac mapping and ablation system 100. This software may be downloaded to processing device(s) 102 in electronic form, over a network, for example, and/or it may be provided on tangible media, such as magnetic or optical media or other nonvolatile memory. For example, enhancement may be made to the cardiac visualization and diagnostic capabilities of the cardiac mapping and ablation system 100 by downloading and installing software modules to processing device(s) 102. In an example, processing device(s) 102 may comprise a general-purpose computer.

The processing device(s) 102 may receive, amplify, filter and/or digitize signals (carrying information or data) from catheter 120, including signals generated by sensors 123, 125, and 126, and electrodes 122 and 124. The signals are received and used by processing device(s) 102 to compute such data as the position and orientation of catheter 120, the temperature of catheter 120, as well as the electrical characteristics and/or temperature of tissues in the heart chamber. In an example, appropriate circuitry may be associated with catheter 120 so that processing device(s) 102 receive signals that are already amplified, filtered and/or digitized.

Processing device(s) 102 may also be used to generate and send signals, containing information or instructions, to other elements in cardiac mapping and ablation system 100. For example, processing device(s) 102 may generate and send data and instructions for displaying an interactive event timeline on visual display device 116. In another example, processing device(s) 102 may send/receive information to/from local storage 108. In another example, processing device(s) 102 may send signals to catheter(s) 120 to apply RF energy provided by energy source 119 to an ablation target.

As explained above, processing device(s) 102 may implement specific functions, which may be represented (e.g., illustratively or physically) as separate units within the processing device(s) 202. For example, the processing device(s) 202 may include a decoder unit 104 (e.g., implemented in hardware as a processing circuit and/or software as a software module) that may be configured to receive signals from sensors in catheter 120, and may use the signals to calculate position, orientation, distance, temperature and/or electrocardiogram (ECG) values for catheter distal tip 128.

In another example, processing device(s) 102 may include a controller unit 107 for sending instructions to other devices in cardiac mapping and ablation system 100. For example, controller unit 107 may send instructions to energy source 119 to provide RF energy to catheter(s) 120 for ablation, and may send instructions to catheter(s) 120 to apply the RF energy to an ablation target (e.g., one or more locations along a path).

Figure 3:
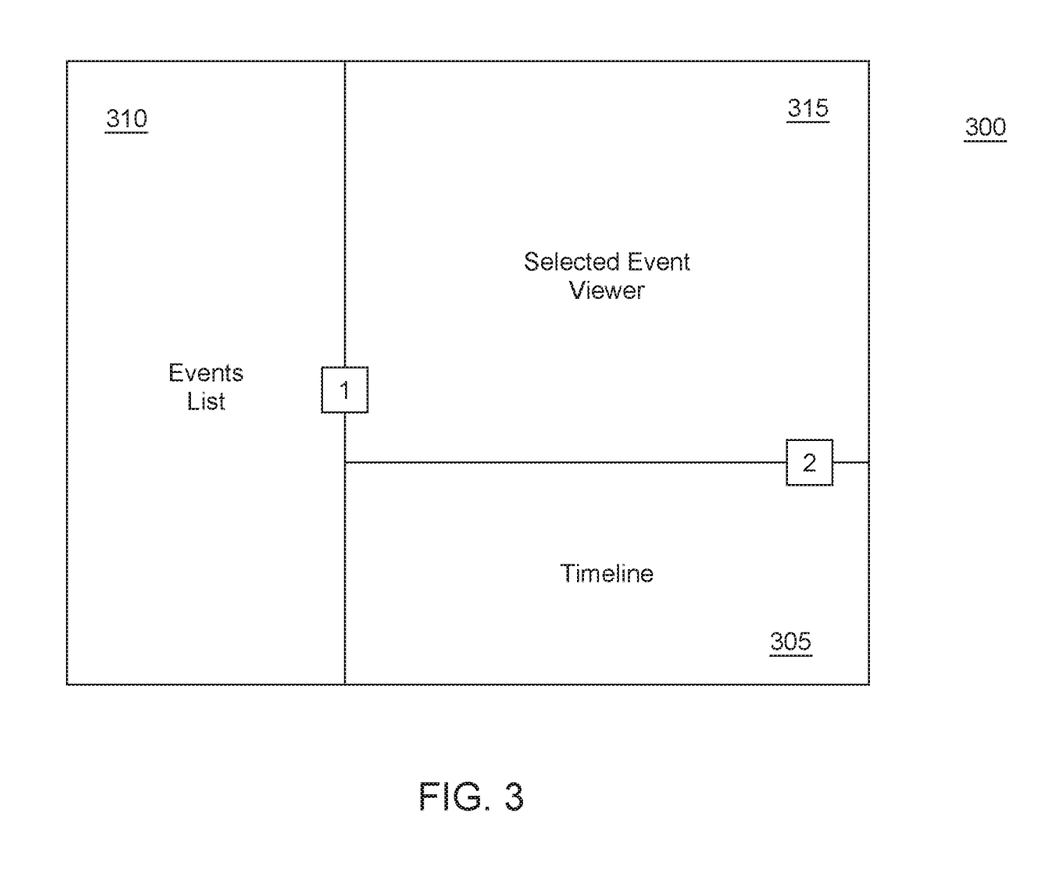
FIG. 3 is a schematic diagram of an event viewer in accordance with certain implementations.

In another example, processing device(s) 102 may include an event viewer unit 106 (e.g., implemented in hardware as processing circuits and/or software as a software module) that may be configured to collect event data, signal indicators, image data and other data, information and signals generated by sensors 123, 125, and 126, and electrodes 122 and 124, for example. For example, event data can include, but is not limited to, tags, user generated points, ablation events, and other like events. Event viewer unit 106 may use the collected event data and signal indicators to generate multiple visual representations of the collected event data and signal indicators, where each visual representation is correlated with the other visual representations. FIG. 3 is a schematic illustration of an event viewer 300 having three visual representations including an interactive event timeline viewer 305, an events list viewer 310 and a selected event viewer 315. Event viewer 300 can be displayed on visual display device 116, for example. Further details with respect to FIG. 3 are described herein.

The processing units 104, 106 and 107 are examples, and do not comprise all the possible functions that may be implemented in processing device(s) 102. Other functionality and/or processing units may be included in processing device(s) 102 but are not shown.

Visual display device 116 may be used to display event data, signal indicators, image data, information and signals, visual representations and/or maps of the heart and show the exact location and orientation of catheter 120 within the heart based on information processing done in processing device(s) 102. For example, maps may be displayed in selected event viewer 315 as anatomical maps, cardiac electrical activation maps, cardiac electrical propagation maps, cardiac electrical potential maps, impedance maps, cardiac chamber geometry, and ECG fragmentation maps. In addition to the cardiac representations/maps and catheter(s), other objects in view and/or information (e.g., labels, diagnostics etc.) relevant to the mapping, diagnostic and therapeutic procedures may also be displayed in interactive event timeline viewer 305 and events list viewer 310 on visual display device 116. Interactive event timeline viewer 305 allows an operator, physician or user (collectively "user") to see temporal relationships between the captured events. The user can see, for example, simultaneous events, long duration events versus short duration events, continuous events and specific event types as described herein.

User interface(s) 118 may be used by one or more users or operators to interact with and control cardiac mapping and ablation system 100. User interface(s) 118 may include, but are not limited to include, the following devices: a keyboard; a touch-sensitive display; and/or a mouse. User interface(s) 118 may allow operators to access and manipulate visual information, and may provide them with the ability to change views, and tag and/or label lesions to keep track of treatment strategies for individual patients. For example, user interface(s) 118 allows a user to manipulate interactive event timeline viewer 305, events list viewer 310 and selected event viewer 315 as described herein.

Users of cardiac mapping and ablation system 100 may include, but are not limited to include, the following: a physician (e.g., an electrophysiologist) who may, for example, control the catheter, gather and interpret diagnostics, and perform the ablation procedure; and a Clinical Application Specialist (CAS) who functions as the physician's assistant during the procedures.

During the operation of a cardiac mapping and ablation system, such as the cardiac mapping and ablation system 100 in FIG. 1, vast amounts of data are captured including event data and signals from electrodes and sensors used during a medical procedure. A user, such as a physician, needs to be able to focus on specific times of interest in the medical procedure and analyze what happened before and after the time of interest. In particular, the user needs to be able to easily and at a glance discern from the collected event data the temporal relationship between multiple events including, but not limited to, which events may have occurred simultaneously, the duration of an event as compared to other events, and the time difference between events.

Described herein is a system and method for providing an interactive event timeline that allows a user to highlight critical events in terms of time, ECG context, and event type, for example. The user can easily and quickly navigate, understand, mark, and retroactively define key points of interest to improve accuracy and patient outcomes.

Figure 4:
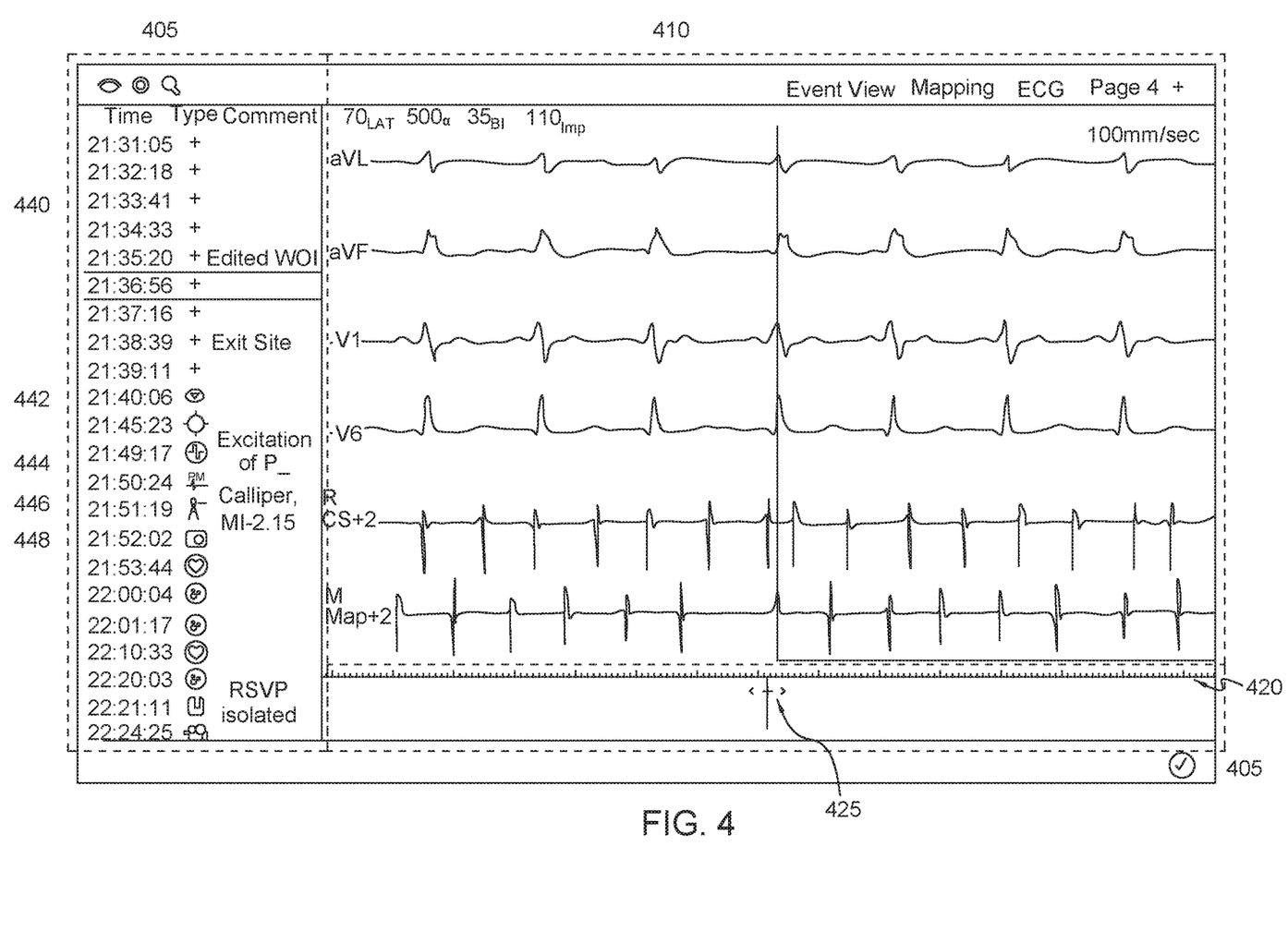
FIG. 4 is an example event viewer in accordance with certain implementations.
Figure 5:
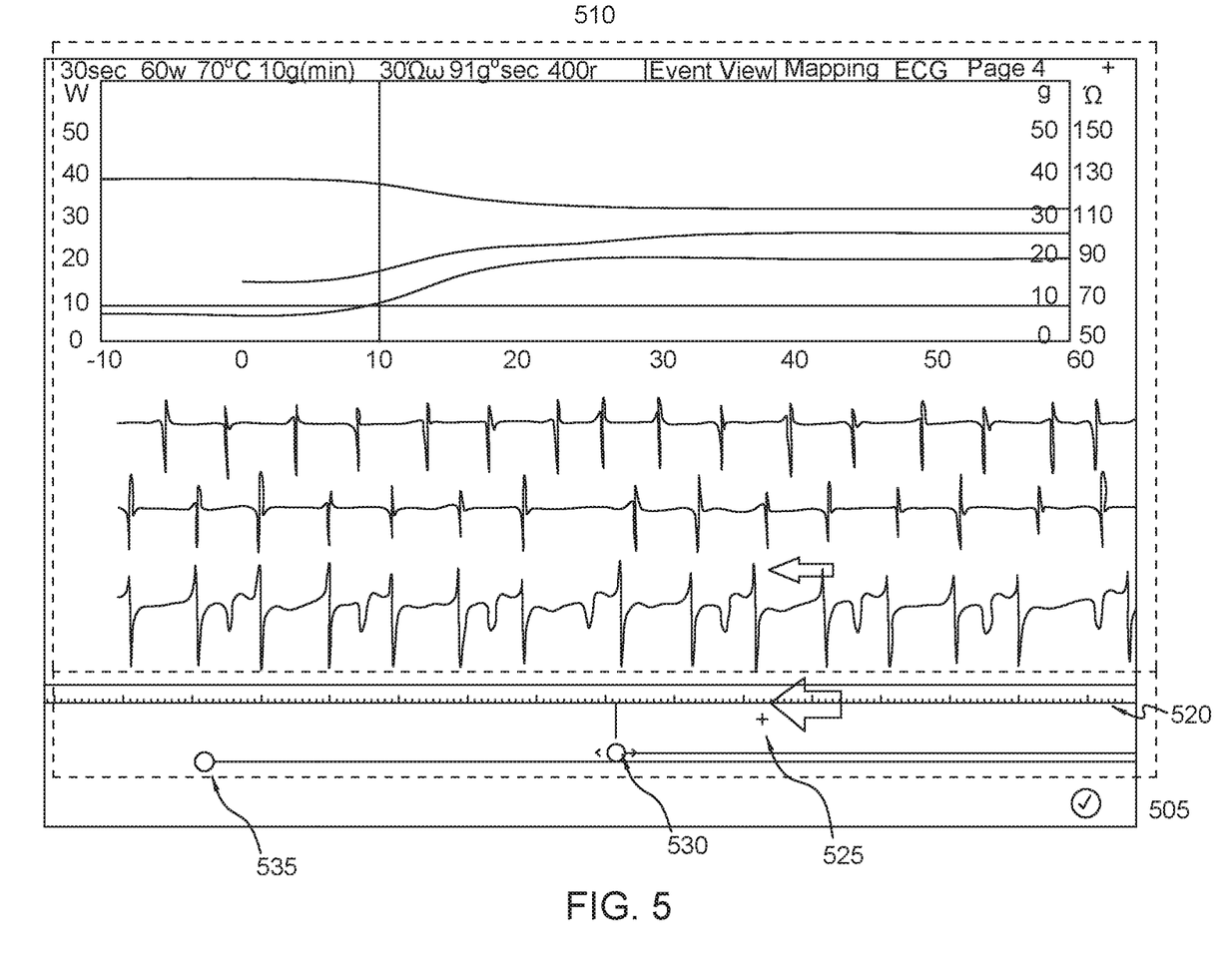
FIG. 5 is another example event viewer in accordance with certain implementations.

As noted earlier, FIG. 3 illustrates event viewer 300 with interactive event timeline viewer 305, events list viewer 310 and selected event viewer 315. Event viewer 300 can be displayed on visual display device 116, for example. FIG. 4 shows a picture of an example event viewer 400 with interactive event timeline viewer 405, events list viewer 410 and selected event viewer 415. FIG. 5 shows a picture of an example event viewer 500 with interactive event timeline viewer 505 and selected event viewer 515.

Each of interactive event timeline viewer 305, events list viewer 310 and selected event viewer 315 are correlated with one another. That is, a selection in any one of interactive event timeline viewer 305, events list viewer 310 and selected event viewer 315 can result in a corresponding selection in the other ones of interactive event timeline viewer 305, events list viewer 310 and selected event viewer 315. This can be done using user interface 118, for example. Each viewer will at least show the time selected, or the time of the event selected.

Interactive event timeline viewer 305 is configured to display a procedure timeline(s) based on and generated from the captured event data by event viewer unit 106, for example. In particular, interactive event timeline viewer 305 can depict tags, user generated points, ablation events with start and stop times, pacing events with start and stop times, continuous events, discrete events, and other event types. The events may be shown in overlap fashion, using multiple colors and/or icons. For example, interactive event timeline viewer 405 depicts a continuous procedure timeline 420 and a user point 425. In another example, interactive event timeline viewer 505 depicts a continuous procedure timeline 520, a user point 525, a tag 530 and an ablation event 535.

A user can select a time on the displayed timeline(s) or select any denoted event(s) in interactive event timeline viewer 305 to zoom in on the specific time to see what events occurred at that time or what the ECG signals are that time or during that event. A corresponding event in events list viewer 310 and selected event viewer 315 is then highlighted. For example, in FIG. 4 a point 450 is highlighted in association with selected point 425 in interactive event timeline viewer 405 and a set of ECGs are displayed in selected event viewer 415. A user can then annotate the selected time or event for further or future review. In an implementation, a user can selected a range of time centered on a time of interest on the displayed timeline(s) to see what happens before or after the time of interest. Selection of a range of time can highlight all events captured during the selected time range.

A timescale of the displayed timeline(s) can vary depending on level of zoom. In an implementation, displaying of certain event types may be dependent on the zooming factor or timescale being used.

In an implementation, a user can scroll along the displayed timeline(s). Scrolling along the displayed timeline(s) can cause a corresponding movement in selected event viewer 315. that is, if the user is scrolling along the timeline, the highlighted or demarked portions of an ECG signal, for example, will move in unison. Similarly, scrolling along the timeline will cause which events are highlighted on events list viewer 310 to change accordingly.

Events list viewer 310 is configured to display a vertical list of events that occurred during a procedure. For example, events list viewer 410 shows user points 440, ultrasound contour 442, pacing session 444, ablation events, caliper 446, still image 448 and other events. A user can select a listed event, which in turn causes interactive event timeline viewer 305 and selected event viewer 315 to display corresponding data or information.

Selected event viewer 315 is configured to display ECGs, 3D heart maps and other electrode or sensor signal data in response to selection of a time or an event in interactive event timeline viewer 305 or events list viewer 310.

A physical relationship between each of interactive event timeline viewer 305, events list viewer 310 and selected event viewer 315 may be controlled by selecting and moving an area separator(s) such as for example, area separator 1 and area separator 2. That is, a viewing area of each of interactive event timeline viewer 305, events list viewer 310 and selected event viewer 315 is adjustable. In an implementation, viewer controllers are provided to expand or collapse any one of interactive event timeline viewer 305, events list viewer 310 and selected event viewer 315. For example, FIG. 5 shows event viewer 500 with a collapsed events list viewer. Viewer controllers can be, but are not limited to, buttons, icons, pull-down menus and the like.

Figure 6:
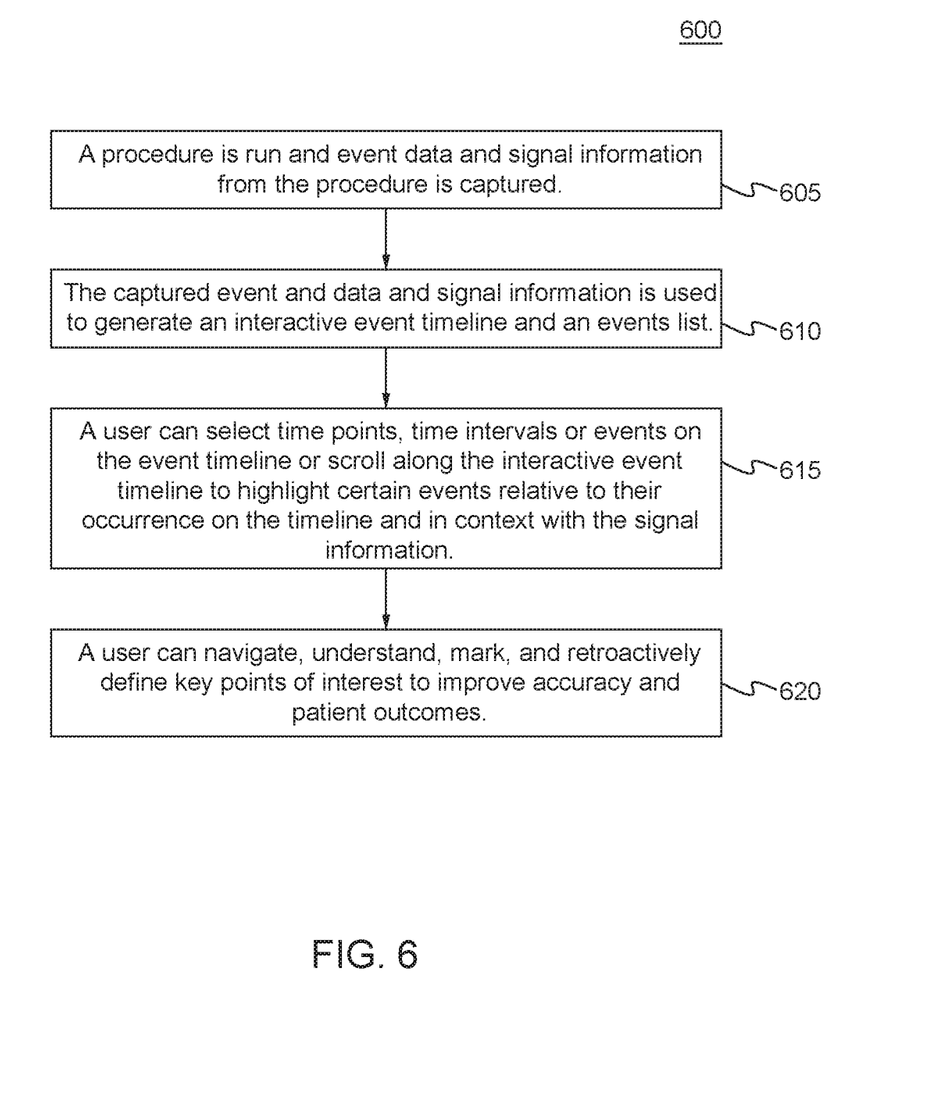
FIG. 6 is a flow chart for using an interactive event timeline in accordance with certain implementations.

FIG. 6 is a flowchart 600 for using an interactive event timeline in accordance with certain implementations. A procedure is run and event data and signal information from the procedure is captured (605). The captured event and data and signal information is used to generate an interactive event timeline and an events list (610), where the interactive event timeline shows temporal relationships between the events that are captured during the procedure. A user can select time points, time intervals or events on the event timeline or scroll along the interactive event timeline to highlight certain events relative to their occurrence on the timeline and in context with the signal information (615). A user can navigate, understand, mark, and retroactively define key points of interest to improve accuracy and patient outcomes (620).

In general, a method for interactive event timeline processing includes capturing event data and signal information during a medical procedure, generating, from the captured event data, at least an interactive event timeline which provides temporal relationships between the captured event data, wherein the interactive event timeline is correlated with an events list and an event view, selecting at least one of a time of interest or an event in the interactive event timeline to highlight certain events relative to an occurrence on the interactive event timeline and in context with the signal information associated with the selected time of interest or even and annotating the selected time of interest or event. In an implementation, the interactive event timeline, the events list and the event view nearly simultaneously depict the selected time of interest or event and the signal information associated with the selected time of interest or event. In an implementation, the interactive event timeline depicts at least simultaneous events, long duration events, short duration events, continuous events, and specific event types. In an implementation, the time of interest is an interval of time. In an implementation, a selected interval of time captures and displays all events that occurred in the selected interval of time. In an implementation, the method further includes providing a temporal indication on the interactive event timeline upon selection of a signal from the signal information displayed on the event viewer. In an implementation, the method further includes changing a temporal resolution of the interactive event timeline to provide different time scopes relative to the medical procedure. In an implementation, the method further includes changing a temporal resolution of the interactive event timeline to provide different time scopes relative to the selected time of interest or event. In an implementation, the captured data includes at least tags, user generated points, pacing events and ablation events.

In general, a system for interactive event timeline processing includes a catheter including at least a plurality of sensors and electrodes, the catheter configured to capture signal information during a medical procedure. The system also includes an event viewer unit configured to capture event data during the medical procedure and receive the captured signal information. The event viewer unit configured to generate, from the captured event data, at least an interactive event timeline which provides temporal relationships between the captured event data. The system also includes a display connected to the event viewer unit. The display configured to display at least the interactive event timeline. The system also includes a user interface connected to the display. The user interface configured to select at least one of a time of interest or an event in the interactive event timeline to highlight certain events relative to an occurrence on the interactive event timeline and in context with the signal information associated with the selected time of interest or event and the user interface configured to annotate the selected time of interest or event. In an implementation, the display is further configured to display an events list and an event view, and where the interactive event timeline, the events list and the event viewer nearly simultaneously depict the selected time of interest or event and the signal information associated with the selected time of interest or event. In an implementation, the interactive event timeline depicts at least simultaneous events, long duration events, short duration events, continuous events, and specific event types. In an implementation, the time of interest is an interval of time. In an implementation, a selected interval of time captures and displays all events that occurred in the selected interval of time. In an implementation, a temporal indication on the interactive event timeline is depicted upon selection of a signal from the signal information displayed on the event viewer. In an implementation, changing a temporal resolution of the interactive event timeline provides different time scopes relative to the medical procedure. In an implementation, changing a temporal resolution of the interactive event timeline provides different time scopes relative to the selected time of interest or event.

In general, a system for interactive event timeline processing includes a catheter configured to capture signal information during a medical procedure, and an event viewer unit configured to capture event data during the medical procedure and receive the captured signal information. The the event viewer unit configured to generate, from the captured event data, at least an interactive event timeline which provides temporal relationships between the captured event data. The system also includes an interactive event timeline viewer configured to receive and display the interactive event timeline and a user interface connected to the interactive event timeline viewer. The user interface configured to select at least one of a time of interest or an event in the interactive event timeline to highlight certain events relative to an occurrence on the interactive event timeline and in context with the signal information associated with the selected time of interest or event. The system also includes an events list viewer configured to receive and display a list of events and an event viewer configured to display the signal information associated with the selected time of interest or event, wherein each of the interactive event timeline viewer, the events list viewer and the events viewer are correlated with one another; and the user interface configured to annotate the selected time of interest or event. In an implementation, the interactive event timeline depicts at least simultaneous events, long duration events, short duration events, continuous events, and specific event types. In an implementation, changing a temporal resolution of the interactive event timeline provides different time scopes relative to at least one of the medical procedure or to the selected time of interest or event.

The disclosures are described herein with respect to cardiac mapping and ablation procedures for the cardiac system, although it is understood by one skilled in the art that the disclosures may be applied to systems and procedures that can be used in any cavity or system in the body, including, but not limited to, the respiratory/pulmonary system, the respiratory and pulmonary system, the digestive system, the neurovascular system, and/or the circulatory system.

The embodiments and procedures described herein may be implemented in hardware, and/or software. A computer system for performing ablation may be capable of running software modules that introduce additional features including the procedures described herein. The procedures described herein may enable advanced cardiac visualization, and diagnostic capabilities to enhance clinicians' ability to diagnose and treat heart rhythm disorders. Although the procedures disclosed herein are describe with respect to ablation procedures relating to the cardiac system, the systems and procedures disclosed herein may be similarly used as part of therapeutic and diagnostic procedures in other parts of the body.

What is claimed is:

1. A method for interactive event timeline processing, the method comprising:
    capturing event data from a patient's body, the event data comprising signal information captured by a catheter during a cardiac ablation medical procedure;
    generating, from the captured event data, at least an interactive event timeline of the cardiac ablation medical procedure which provides temporal relationships between the captured event data;
    receiving an input to the interactive event timeline, from a user interface; selecting at least one of a time of interest or an event in the interactive event timeline based on the input received from the user interface;
    displaying, via a display, the signal information corresponding to the selected at least one of the time of interest or the event;
    annotating the at least one of the time of interest or the event, and
    displaying, via the display, an interactive event timeline viewer configured to receive and display in real-time during the cardiac ablation medical procedure the interactive event timeline, an events list viewer configured to receive and display in real-time during the cardiac ablation medical procedure a list of events occurring during the cardiac ablation medical procedure, and a selected event viewer configured to receive and display in real-time during the cardiac ablation medical procedure the signal information captured by the catheter, the interactive event timeline viewer, the events list viewer, and the selected event viewer being correlated with one another wherein a selection made in one of the interactive event timeline viewer, the events list viewer, and the selected event viewer, will result in a corresponding selection in the other ones of the interactive event timeline viewer, the events list viewer, and the selected event viewer and being displayed in a physical relationship wherein the interactive event timeline viewer is separated from the events list viewer by a first area separator, the selected event viewer is separated from the interactive event timeline viewer by a second area separator, and the events list viewer is separated from the selected event viewer by the first area separator, the first area separator and the second area separator being adjustable in response to an input from the user interface to expand or collapse any one of the interactive event timeline viewer, the events list viewer, and the selected event viewer,
    wherein the interactive event timeline viewer is adjustable to be zoomed in and zoomed out to display a timescale representing only a portion of the interactive event timeline, the timescale being adjustable based upon a level of zoom selected by a user.

2. The method of claim 1, wherein the interactive event timeline viewer, the events list viewer and the selected event viewer depict the selected time of interest or event and the signal information associated with the selected time of interest or event.

3. The method of claim 2, wherein the interactive event timeline viewer depicts at least simultaneous events, long duration events, short duration events, continuous events, and specific event types.

4. The method of claim 1, wherein the time of interest is an interval of time.

5. The method of claim 1, wherein a selected interval of time captures and displays all events that occurred in the selected interval of time.

6. The method of claim 1, further comprising: providing a temporal indication on the interactive event timeline viewer upon selection of a signal from the signal information displayed on the selected event viewer.

7. The method of claim 1, further comprising: changing a temporal resolution of the interactive event timeline to provide different time scopes relative to the cardiac ablation medical procedure.

8. The method of claim 1, further comprising: changing a temporal resolution of the interactive event timeline to provide different time scopes relative to the selected time of interest or event.

9. The method of claim 1, wherein the captured data includes at least tags, user generated points, pacing events and ablation events.

10. A system for interactive event timeline processing, the system comprising:
a catheter including at least a plurality of sensors and electrodes, the catheter configured to capture signal information during a cardiac ablation medical procedure;
a processor configured to capture event data during the cardiac ablation medical procedure based at least on the captured signal information;
the processor configured to generate, from the captured event data, at least an interactive event timeline of the cardiac ablation medical procedure which provides temporal relationships between the captured event data;
a display connected to the processor;
the processor further including an event viewer,
the event viewer including an interactive event timeline viewer configured to receive and display in real-time during the cardiac ablation medical procedure the interactive event timeline, an events list viewer configured to receive and display in real-time during the cardiac ablation medical procedure a list of events occurring during the cardiac ablation medical procedure, and a selected event viewer configured to receive and display in real-time during the cardiac ablation medical procedure the signal information captured by the catheter, the interactive event timeline viewer, the events list viewer, and the selected event viewer being correlated with one another wherein a selection made in one of the interactive event timeline viewer, the events list viewer, and the selected event viewer, will result in a corresponding selection in the other ones of the interactive event timeline viewer, the events list viewer, and the selected event viewer,
the display configured to display the interactive event timeline viewer, the events list viewer, and the selected event viewer in a physical relationship wherein the interactive event timeline viewer is separated from the events list viewer by a first area separator, the selected event viewer is separated from the interactive event timeline viewer by a second area separator, and the events list viewer is separated from the selected event viewer by the first area separator, the first area separator and the second area separator being adjustable in response to an input by a user interface to expand or contract any one of the interactive event timeline viewer, the events list viewer, and the selected event viewer, wherein the interactive event timeline viewer is adjustable to be zoomed in and zoomed out to display a timescale representing only a portion of the interactive event timeline, the timescale being adjustable based upon a level of zoom selected by a user; the user interface connected to the display,
the user interface configured to select at least one of a time of interest or an event in the interactive event timeline to highlight certain events relative to an occurrence on the interactive event timeline and in context with the signal information associated with the selected time of interest or event; and,
the user interface configured to annotate the selected time of interest or event.

11. The system of claim 10, wherein the interactive event timeline viewer, the events list viewer and the selected event viewer depict the selected time of interest or event and the signal information associated with the selected time of interest or event.

12. The system of claim 11, wherein the interactive event timeline viewer depicts at least simultaneous events, long duration events, short duration events, continuous events, and specific event types.

13. The system of claim 10, wherein the time of interest is an interval of time.

14. The system of claim 10, wherein a selected interval of time captures and displays all events that occurred in the selected inters al of time.

15. The system of claim 10, wherein a temporal indication on the interactive event timeline viewer is depicted upon selection of a signal from the signal information displayed on the selected event viewer.

16. The system of claim 10, wherein changing a temporal resolution of the interactive event timeline viewer provides different time scopes relative to the cardiac ablation medical procedure.

17. The system of claim 10, wherein changing a temporal resolution of the interactive event timeline viewer provides different time scopes relative to the selected time of interest or event.

* * * * *

UNITED STATES PATENT AND TRADEMARK OFFICE
CERTIFICATE OF CORRECTION

PATENT NO. : 11,295,835 B2
APPLICATION NO. : 15/823164
DATED : April 5, 2022
INVENTOR(S) : Moshe Ingel et al.

It is certified that error appears in the above-identified patent and that said Letters Patent is hereby corrected as shown below:

In the Specification

In Column 2, Line 11, delete "example" and insert -- example of --, therefor.
In Column 7, Line 2, delete "user point 425." and insert -- user point 440. --, therefor.
In Column 7, Line 16, delete "selected" and insert -- select --, therefor.
In Column 9, Line 20, delete "The the" and insert -- The --, therefor.

In the Claims

In Column 10, Line 19, in Claim 1, delete "event, and" and insert -- event; and --, therefor.
In Column 12, Line 22, in Claim 10, delete "event; and," and insert -- event, and --, therefor.
In Column 12, Line 38, in Claim 14, delete "inters al" and insert -- interval --, therefor.

Signed and Sealed this
Tenth Day of September, 2024

Katherine Kelly Vidal
*Director of the United States Patent and Trademark Office*